(12) United States Patent
Veatch

(10) Patent No.: US 10,045,865 B2
(45) Date of Patent: Aug. 14, 2018

(54) JOINT AND DIGIT

(71) Applicant: Invisible Hand Enterprises, LLC, Westminster, CO (US)

(72) Inventor: Bradley Delton Veatch, Westminster, CO (US)

(73) Assignee: INVISIBLE HAND ENTERPRISES, LLC, Westminster, CO (US)

( * ) Notice: Subject to any disclaimer, the term of this patent is extended or adjusted under 35 U.S.C. 154(b) by 0 days.

(21) Appl. No.: 15/276,753

(22) Filed: Sep. 26, 2016

(65) Prior Publication Data

US 2017/0014246 A1  Jan. 19, 2017

Related U.S. Application Data

(62) Division of application No. 14/205,997, filed on Mar. 12, 2014, now Pat. No. 9,474,630.

(60) Provisional application No. 61/777,024, filed on Mar. 12, 2013.

(51) Int. Cl.
*A61F 2/58* (2006.01)
*A61F 2/68* (2006.01)
*A61F 2/50* (2006.01)

(52) U.S. Cl.
CPC ............. *A61F 2/586* (2013.01); *A61F 2/583* (2013.01); *A61F 2/68* (2013.01); *A61F 2002/5093* (2013.01)

(58) Field of Classification Search
CPC .. A61F 2/54; A61F 2/583; A61F 2/586; A61F 2002/5016; A61F 2002/5038; A61F 2002/5039; A61F 2002/5041; A61F 2002/5043; A61F 2002/5093; A61F 2002/5095; A61F 2002/5096; A61F 2002/5098; A61F 2005/0134; A61F 2005/0137; A61F 2005/0146; A61F 2005/0148; A61F 2005/0151; A61F 2005/0153; A61F 5/013; A61H 3/46
See application file for complete search history.

(56) References Cited

U.S. PATENT DOCUMENTS

| | | |
|---|---|---|
| 450,476 A | 4/1891 | Sparham |
| 797,335 A | 8/1905 | Taylor |
| 984,179 A | 2/1911 | Aydt |
| 1,225,415 A | 5/1917 | Cronemiller |
| 1,277,747 A | 5/1917 | O'Connor |
| 1,298,502 A | 3/1919 | Henning |
| 1,301,575 A | 4/1919 | Kraczynski |
| 1,304,099 A | 5/1919 | Robinson |

(Continued)

OTHER PUBLICATIONS

Pauline. Funky Friends Factory Button Jointing for Beginners. Sep. 14, 2010.*

(Continued)

*Primary Examiner* — Thomas J Sweet
*Assistant Examiner* — Christie Bahena
(74) *Attorney, Agent, or Firm* — IP Alternative, LLC

(57) ABSTRACT

This disclosure relates to the field of prosthetics, more specifically to a pinless anthropomorphic hinge or joint, and a digit comprising one or more phalanges connected by and articulating around pinless joints, whereby the joints provide compliant movement in more than one plane. This disclosure also relates to modular prosthetic systems comprising multiple digits, in particular for partial-hand replacements.

5 Claims, 14 Drawing Sheets

(56) References Cited

U.S. PATENT DOCUMENTS

| | | |
|---|---|---|
| 1,377,956 A | 5/1921 | Anderson |
| 1,380,835 A | 7/1921 | Pecorella et al. |
| 1,422,714 A | 7/1922 | Ingold |
| 1,484,913 A | 2/1924 | Surry |
| 1,501,308 A | 7/1924 | Burney |
| 1,507,680 A | 9/1924 | Pecorella et al. |
| 1,608,689 A | 11/1926 | Apel |
| 1,742,269 A | 1/1930 | McElroy |
| 2,259,911 A | 10/1941 | Tancred et al. |
| 2,285,885 A | 6/1942 | Becker |
| 2,364,313 A | 12/1944 | Pecorella |
| 2,422,302 A | 6/1947 | Horn |
| 2,425,154 A | 8/1947 | Hibbard |
| 2,429,001 A | 10/1947 | Stone |
| 2,435,614 A | 2/1948 | Tureman |
| 2,457,305 A | 12/1948 | Dale |
| 2,486,746 A | 11/1949 | Jinkins |
| 2,497,493 A | 2/1950 | Edwards |
| 2,500,614 A | 3/1950 | Lohman |
| 2,545,947 A | 3/1951 | Felip et al. |
| 2,549,074 A | 4/1951 | Fishbein et al. |
| 2,556,524 A | 6/1951 | Drennon |
| 2,567,066 A | 9/1951 | Goldman |
| 2,847,678 A | 8/1958 | Opuszenski |
| 3,090,049 A | 3/1963 | Lanteigne |
| 3,188,753 A | 6/1965 | Lovercheck |
| 3,345,647 A | 10/1967 | Gentiluomo |
| 3,509,583 A | 5/1970 | Fraioli |
| 3,694,021 A | 9/1972 | Mullen |
| 4,193,139 A | 3/1980 | Walker |
| 4,246,661 A | 1/1981 | Pinson |
| 4,364,593 A | 12/1982 | Maeda |
| 4,466,800 A | 8/1984 | Breiden |
| 4,792,338 A | 12/1988 | Rennerfelt |
| 4,834,761 A | 5/1989 | Walters |
| 4,865,376 A | 9/1989 | Leaver et al. |
| 4,944,758 A | 7/1990 | Bekki et al. |
| 4,955,918 A | 9/1990 | Lee |
| 5,062,855 A | 11/1991 | Rincoe |
| 5,080,681 A * | 1/1992 | Erb .......................... A61F 2/583 294/111 |
| 5,200,679 A | 4/1993 | Graham |
| 5,245,885 A | 9/1993 | Robertson |
| 5,326,369 A | 7/1994 | Schectman |
| 5,447,403 A | 9/1995 | Engler |
| 5,647,723 A | 7/1997 | Rush |
| 6,517,132 B2 | 2/2003 | Matsuda et al. |
| 6,817,641 B1 | 11/2004 | Singleton |
| 6,908,489 B2 | 6/2005 | Didrick |
| 6,913,627 B2 | 7/2005 | Matsuda |
| 7,361,197 B2 | 4/2008 | Winfrey |
| 7,655,051 B2 | 2/2010 | Stark |
| 8,177,856 B2 | 5/2012 | Jaworski |
| 8,231,158 B2 | 7/2012 | Dollar et al. |
| 2004/0054424 A1 | 3/2004 | Matsuda |
| 2006/0212129 A1 | 9/2006 | Lake et al. |
| 2006/0224249 A1 * | 10/2006 | Winfrey .................. A61F 2/583 623/64 |
| 2008/0188952 A1 | 8/2008 | Veatch et al. |
| 2011/0144770 A1 | 6/2011 | Moyer et al. |
| 2012/0203358 A1 | 8/2012 | Lind et al. |

OTHER PUBLICATIONS

Needle and Clay. Experimental Dollmaking. May 9, 2008.*
Barbie Legs. Science NetLinks. 1999.*

* cited by examiner

JOINT AND DIGIT

CROSS REFERENCE TO RELATED APPLICATIONS

The present application claims the benefits of U.S. Provisional Patent Application No. 61/777,024, filed Mar. 12, 2013, of the same title, which is incorporated herein by this reference in its entirety. The present application is a divisional application of U.S. Non-provisional patent application Ser. No. 14/205,997, which has issued as U.S. Pat. No. 9,474,630.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. 1R43HD07051401 awarded by the National Institutes of Health.

TECHNICAL FIELD

This disclosure relates to the field of prosthetics, more specifically to a pinless anthropomorphic hinge or joint, and a digit comprising one or more phalanges connected by and articulating around pinless joints, whereby the joints provide compliant movement in more than one plane. This disclosure also relates to modular prosthetic systems comprising multiple digits, in particular for partial-hand replacements.

BACKGROUND

The following text should not be construed as an admission of knowledge in the prior art. Furthermore, citation or identification of any document in this application is not an admission that such document is available as prior art to the present disclosure, or that any reference forms a part of the common knowledge in the art.

A fundamental challenge in the field of prosthetic device development is to find a design that balances functionality with cost. The amputee desires a prosthetic device that both mimics and feels like the natural component that has been lost, for example, a finger or a hand. The replacement device must also be affordable. This need for cost effective prosthetic appliances is especially prevalent in poor countries and those suffering from civil war or natural disasters, such as Haiti or several African nations such as Sierra Leone, Uganda, and Kenya.

The human hand is an amazingly complicated feat of engineering, and very difficult to emulate. Even individual human fingers have an incredible range of motion and dexterity. This is especially evident when watching the fine motor skills of a sculptor, guitarist or surgeon. These motions are very difficult to mimic with an artificial device, especially in a cost-effective manner. In general, the engineering designs that most successfully mimic nature are also the most expensive. These designs can be described as "bionic", usually costing thousands of dollars to manufacture and maintain, or they are destined to remain relegated to the laboratory or to be used only by the most wealthy. The vast majority of people in need of affordable prosthetic devices lack the means to acquire these technologically sophisticated designs. Wonderful engineering feats in themselves, most bionic designs are not economically viable solutions for the masses. However, the other extreme is also lacking. More affordable prosthetic appliance designs tend to have short life spans, high failure rates, and are often expensive or difficult to maintain. From the amputee's perspective, these cheaper designs also tend to provide much less functionality and utility. It is one objective of the present disclosure to provide a prosthetic design that offers a balance of affordability and functionality.

A fundamental element of any prosthetic device that provides motion, for example an artificial arm, hand or finger, is a joint. Without one or more joints, a finger is simply a lever with severely limited functionality. Joints provide the means needed to flex or extend the digit, allowing for control to pick-up and grasp objects, ranging from such things as a hammer to a delicate wine glass.

Despite their importance, viable prosthetic joint designs are surprisingly limited, the vast majority relying on a pin that rigidly restricts motion to revolution about a single axis. Although simple in concept, "pin joints" do not mimic their natural counterparts, which are held together by a number of flexible ligaments. Knees, elbows, wrists, and fingers all rely upon ligaments for motion, typically biased to one plane but having some ability to move in all three spatial dimensions, including some rotational motion around an axis. Pins, on the other hand, limit motion to pure rotation, thus giving prosthetic appliances an artificial, rigid, and almost robotic motion.

Nevertheless, history has shown a propensity and preference for the pin (or screw, nail, rod, peg, or pinion). U.S. Pat. No. 1,608,689 (issued in 1926), describes an artificial hand comprising fingers and a thumb. The phalanges of each digit are held to their adjacent neighbors using pins.

U.S. Pat. No. 1,742,269 (1930) resorts to the same solution for providing a pivot point between opposing phalanges: pins.

Many more modern joint and prosthetic designs also use pins as the fundamental elements for providing motion between adjacent phalanges. Examples include: U.S. Pat. No. 5,326,369; U.S. Patent Application Publication No. 2004/0054424; U.S. Pat. App. Pub. No. 2006/0212129; U.S. Pat. No. 7,361,197; U.S. Pat. No. 7,655,051; U.S. Pat. App. Pub. No 2012/0203358.

Some different approaches do exist. An example from the WWII era is U.S. Pat. No. 2,500,614 which issued in 1948. This patent discloses a "ball and socket" system for the joints in an artificial hand. However, this solution poses significant manufacturing difficulties and is decidedly more complex in operation than simple pins.

Another prosthetic joint from this era is U.S. Pat. No. 2,549,074 which issued in 1951. Instead of pins, this patent discloses a joint comprising a flat metal sheet. This sheet connects the adjacent ends of the two phalanges. A space between the two phalanges allows the finger to flex into a closed position. Although different in concept than the more prominently used pin, this sheet metal joint still poses some of the same problems as the pin; it holds the adjacent phalanges rigidly fixed in all planes except that plane defined by flexion and extension.

Other prosthetic joints posing the same problems as highlighted above include U.S. Pat. No. 4,193,139, which discloses a pin-joint concept (1980) and U.S. Pat. No. 4,944,758, which discloses a ball-and-socket concept (1990).

All of these solutions tend to either limit motion to one plane, unlike natural joints, which allow some degree of motion in all three dimensions, including rotational movement around the digit's axis, or they require potentially more complicated and costly means for manufacturing and maintenance. It is the aim of this disclosure to overcome these problems, with a design that is simple, compact, waterproof, inexpensive, and easy to maintain.

SUMMARY

The present disclosure relates to novel and unique prosthetic joints, and digits comprising these joints. The joints are characterized by their unique lack of pins or nails to secure opposing ends of two phalanges together, and by the joint's ability to more accurately mimic the motion of a natural joint comprising ligaments, which allow some motion in all three dimensions. Instead of pins, the present disclosure secures adjacent phalanges using flexible cord that provides both mechanical integrity and strength, but also mimics natural ligaments by providing more natural movement in planes other than the primary plane defined by flexion and extension, including rotational motion around the axis defined by the extended digit. This "pinless" method of securing adjacent phalanges in a way that allows motion that more accurately mimics the motion of a natural human joint, is a novel and unobvious digit and/or phalanges prosthesis securement mechanism and presents a significant contribution to the field of prosthetics.

In one example of the present disclosure, a digit comprises three joints and three phalanges, the adjacent phalanges being secured using a triad of ligament wraps (loops) made from high-strength, low-creep, braided, polymer filament. For each joint, a single filament passes through a hole in a stabilizing cylinder and a hole in each adjoining phalanx (lever), making ten (10) alternating passes around the joint, with the filament ends secured to prevent loosening or slippage. While ten alternating passes are referenced, it will be appreciated that any number of passes may be used depending on the application. Multiple filament passes form a composite bundle having a tensile strength exceeding that of the phalanx material. This triad construction admits planar flexion-extension movement while limiting lateral, off-axis bending and axial twist to levels consistent with the anatomical finger. Some lateral bend and axial twist, this motion being called circumduction, are desirable as they help distribute tractive forces over the surface of objects, significantly increasing grasp quality.

These and other advantages will be apparent from the disclosure of the aspects, embodiments, and configurations contained herein.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

As used herein, "cylinder" is referred to as a hollow body comprising a circular cross section with parallel sides, slightly concave sides, or slightly convex sides. Therefore, a cylinder is used herein, comprises a hole that passes through the circular cross-sectional area. In the present disclosure, a cylinder provides mechanical stabilization to the joint, and thus is also referred to as a stabilizing cylinder.

The term "extension" refers to when a digit is straight, under the influence of an extending force. As used herein, the term "flexion" refers to when any or all of the joints are rotated, putting the digit into a curl position under the influence of a flexing force.

As used herein, "loop" refers to a cord, filament, cable, wire, thread, line, yarn, string, or fiber, wherein the two ends of such a cord are secured into a circular loop. Alternatively, this cord, filament, cable, etc., may loop multiple times to form a composite loop. A loop simulates a ligament in the present disclosure.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves. As used herein, "phalange" refers to a phalangeal segment, phalanx, digit segment, or lever. So, for the example of the human finger, a "phalange" refers to the proximal, intermediate and distal bones.

As used herein, "nip" refers to an empty space with its boundaries defined by the palmar or volar surfaces of two adjacent phalanges. By way of example, placing two rectangular blocks end-to-end provides no space between. However, rounding the palmar edges of the adjacent blocks provides space between two convex arcs. As used in the context of this disclosure, this space is referred to as a "nip".

As used herein, "plastic" refers to any of various organic compounds produced by polymerization, capable of being molded, extruded, cast into various shapes and films, or drawn into filaments used as textile fibers. A plastic can either be a thermosetting polymer or a thermoplastic polymer. Specifically, the plastic can include acetals, acrylics, acrylonitrile-butadiene-styrene, alkyds, coumarone-indene, diallyl phthalate, epoxy, fluoropolymer, melamine-formaldehyde, nitrile resins, nylon, petroleum resins, phenolics, polyamide-imide, polyarylates, polybutylene, polycarbonate, polyethylene, polyimides, polyphenylene oxide, polyphenylene sulfide, polypropylene, polystyrene, polyurethanes, polyvinyl acetate, styrene acrylonitrile, styrene butadiene latexes, sulfone polymers, thermoplastic polyester, unsaturated polyester, urea-formaldehyde, hexachloroethane, or a combination thereof. More specifically, the plastic can include polyethylene terephthalate (PET or PETE), high-density polyethylene (HDPE), low-density polyethylene (LDPE), polypropylene (PP), polystyrene (PS), nylon, or a combination thereof. The plastic can optionally include one or more additives. The term "plastic" should also be understood to include additives used to enhance the behavioral characteristics of the primary constituent material. Examples include glass fibers, carbon fibers, nanomaterials, hollow spheres, pigments, foaming agents, etc.

As used herein, "thermoset" refers to a polymer that solidifies or "sets" irreversibly when heated. Thermosets are valued for their durability and strength and are used primarily in automobiles and construction.

As used herein, "thermoplastic" refers to a polymer in which the molecules are held together by weak secondary bonding forces that soften when exposed to heat and return to its original condition when cooled back down to room temperature. When a thermoplastic is softened by heat, it can then be shaped by extrusion, molding or pressing. Examples of thermoplastics include polyethylene used in packaging, electrical insulation, milk and water bottles, packaging film, house wrap, and agricultural film; polypropylene used in carpet fibers, automotive bumpers, microwave containers, and external prostheses.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below. Also, while the disclosure is presented in terms of exemplary embodiments, it should be appreciated that individual aspects of the disclosure can be separately claimed.

BRIEF DESCRIPTION OF DRAWINGS

The accompanying drawings are incorporated into and form a part of the specification to illustrate examples of the aspects, embodiments, or configurations disclosed herein. These drawings together with the description, explain the principle of the aspects, embodiments, or configurations. The drawings simply illustrate preferred and alternative examples of how the aspects, embodiments, or configurations can be made and used and are not to be construed as limiting the aspects, embodiments, or configurations to only the illustrated and described examples. Further features and advantages will become apparent from the following, more detailed, description of the various aspects, embodiments, or configurations, as illustrated by the drawings referenced below.

REFERENCE NUMERALS

Figure 1:
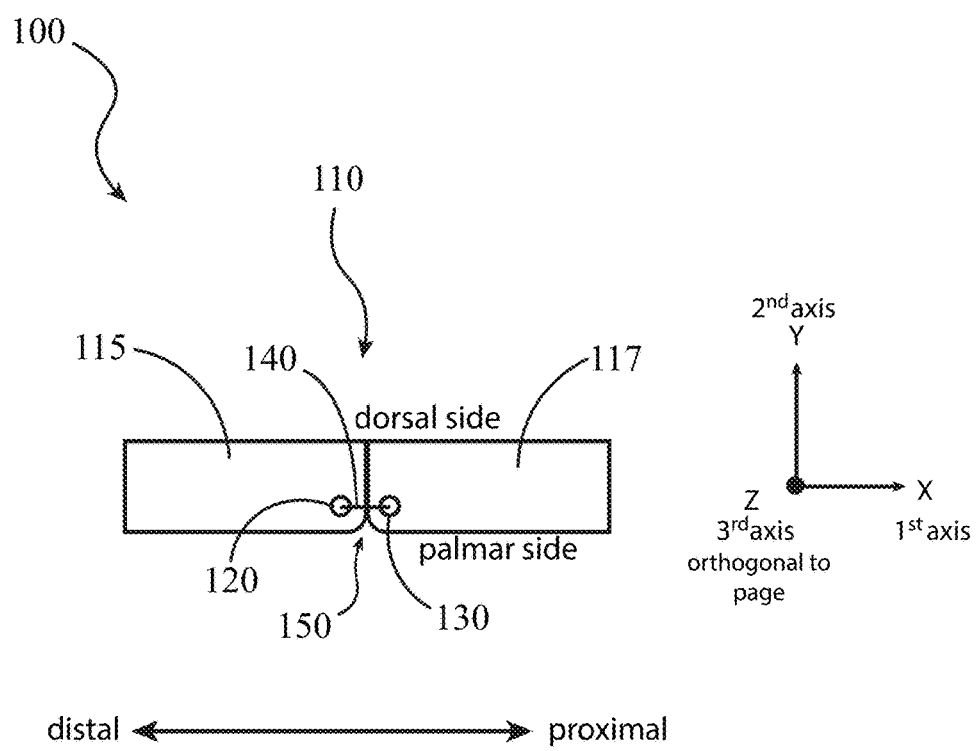
FIG. 1 is a front elevation view of one embodiment of the present disclosure, of a joint of a single loop.

100 . . . digit
110 . . . joint
115 . . . distal lever
117 . . . proximal lever
120 . . . first hole
130 . . . second hole
140 . . . first loop
150 . . . nip
160 . . . second loop
170 . . . third loop
180 . . . cylinder
190 . . . third hole
195 . . . triad
300 . . . digit
310 . . . third lever
320 . . . base
330 . . . fourth hole
340 . . . anchor
350 . . . attachment
400 . . . digit
410 . . . tension guide
420 . . . tension cord
430 . . . tension restraint
440 . . . tension hole
450 . . . fifth hole
460 . . . actuator guide
470 . . . actuator cord
480 . . . actuator hole
490 . . . actuator lead
500 . . . digit
610 . . . flange
700 . . . flange
800 . . . artificial hand
810 . . . ring

DETAILED DESCRIPTION

The following detailed description illustrates the disclosure by way of example and not by way of limitation. This description will clearly enable one skilled in the art to make and use the disclosure, including what is presently believed to be the best mode of carrying out the disclosure.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The present disclosure relates to novel and unique prosthetic joints, and digits comprising these joints, as well as modular prosthetic systems comprising multiple digits, in particular for partial-hand replacements. The joints are characterized by their unique lack of pins, screws or nails to secure opposing ends of two phalanges together, and by the joint's ability to more accurately mimic the motion of a natural joint comprising ligaments, which allow some motion in all three dimensions, a capability called digit circumduction. Instead of pins, the present disclosure secures adjacent phalanges using flexible cord that provides both mechanical integrity and strength, but also mimics natural ligaments by providing more natural movement in planes other than the primary plane defined by flexion and extension, including rotational motion around the axis defined by the extended digit.

Turning to FIG. 1, some embodiments of the present disclosure have a digit 100 and a joint 110 comprising a distal lever 115 and a proximal lever 117, in which the two levers (115 and 117) are aligned lengthwise along a first reference axis, the horizontal X-axis. Each lever (115 and 117) comprises a proximal end and a distal end. The joint 110 connects the proximal end of the distal lever 115 to the adjacent distal end of the proximal lever 117. The levers (115 and 117) are also defined by the vertical Y-axis, and the axis orthogonal to the X- and Y-axis, the Z-axis. The upper surface of the levers (115 and 117), in the Y-axis, is defined as the dorsal side. The lower surface of the levers (115 and 117), also in the Y-axis, is defined as the palmar side. The palmar sides of the adjacent ends of the two levers (115 and 117) are both rounded, across their entire width in the Z-axis direction. Rounding these edges allows for smooth, natural movement when the joint 110 is flexed or extended. Rounding the two opposing edges also forms a space on the palmar side, between the two adjacent levers (115 and 117). This space, referred to as a "nip" 150 has boundaries defined by the rounded edges, which form adjacent convex arcs. The two opposing arcs of the nip 150 move against each other when the joint 110 flexes and extends.

The distal lever 115 contains a first hole 120 that passes through its width in the Z-axis direction. This first hole 120 is preferably located in the proximal end and the palmar half of the distal lever 115. Similarly, the proximal lever 117 has a second hole 130, with this second hole 130 also passing through the width of the proximal lever 117 in the Z-axis direction. The second hole 130 is preferably located in the distal end and the palmar half of the proximal lever 117. The two holes (120 and 130), like the two levers (115 and 117), preferably lay adjacent two each other at about the same height in the Y-axis direction.

The first hole 120 and the second hole 130 in conjunction with a first loop 140, secure the adjacent levers (115 and 117) together, much like ligaments in a natural joint. The first loop 140 comprising a cord, line, filament, etc., passes through the first hole 120 and the second hole 130, forming a complete circular loop that provides the structural stability required of a joint, but also allows for the biased movement in the XY-plane for flexion and extension. However, unlike pin joints, the first loop 140 also provides some flexibility, much like a ligament, to provide some degree of motion in the other dimensions, for example in the YZ-plane and XZ-plane, as well as some rotational motion along the X-axis.

In some embodiments of the present disclosure, the joint 110 provides biased movement in the same direction and plane as the natural appendage being replaced. So, by example, a joint for a prosthetic replacing a finger, will provide biased movement in the XY-plane, whereby flexing will pull the finger downward in the palmar direction, and extension will release the finger back in the dorsal direction.

In some embodiments, the joint 110 limits motion in the XZ-plane to less than 1, 2, 3, 4, or 5 degrees. In some embodiments, the joint 110 limits motion in YZ-plane to less than 1, 2, 3, 4, or 5 degrees.

In some embodiments, the joint 110 limits axial rotation around the X-axis to less than 20, 19, 18, 17, 16, 15, 14, 13, 12, 11, 10, 9, 8, 7, 6, 5, 4, 3, 2, or 1 degree in either or both the clockwise or counter-clockwise directions.

In some embodiments, the distal lever 115, the proximal lever 117 and the first loop 140 are constructed of metal, plastic, ceramic, carbon fiber or a combination thereof. The materials of construction may be the same for all of the components comprising the joint, or each individual element may be constructed from its own unique material, different from the materials chosen for any other element comprising the joint.

In some embodiments, the loop comprises 80# Test, Spectra® by Honeywell, or materials by Innovative Textiles, Inc., or a combination thereof.

In some embodiments of the present disclosure, the distal lever 115 and the proximal lever 117 may be plastic.

In some embodiments of the present disclosure, the levers (115 and 117) may be produced by injection molding.

In some embodiments of the present disclosure, the first loop 140 may comprise plastic, ceramic, carbon fiber, metal wire, or a combination thereof.

In some embodiments of the present disclosure, the first loop 140 comprises a single circular strand, cord, filament, etc. In some embodiments, the first loop 140 comprises more than one circular strand, cord, filament, etc., with each cord passing through both holes (120 and 130) of the joint 110. The number of passes used depends on the strength and structural requirements of the joint being designed and would be known to one skilled in the art.

In some embodiments, the material of construction for the distal lever 115 and the proximal lever 117 comprises aluminum.

Figure 2:
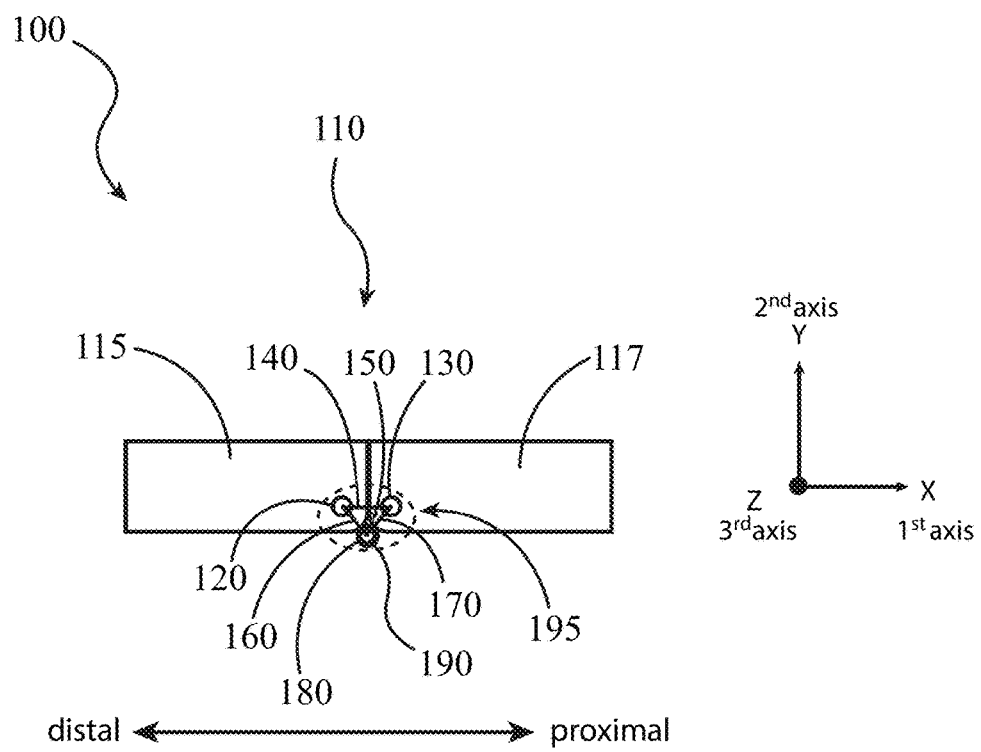
FIG. 2 is a front elevation view of one embodiment of the present disclosure of a joint of three loops.

Referring to FIG. 2, in some embodiments of the present disclosure, the joint 110 of a digit 100 further comprises a stabilizing cylinder 180 that is placed in the nip 150 located on the palmar side of the adjacent ends of the distal lever 115 and the proximal lever 117. This stabilizing cylinder 180 fits in the nip 150 formed by the rounded edges of the two levers (115 and 117), and lays in the Z-axis direction. The width of the stabilizing cylinder 180 may be about the same as the width of the levers (115 and 117) in the Z-axis direction, but may also be a little narrower or a little wider. The two ends of the stabilizing cylinder 180 may be flanged (not shown) to assist with holding the stabilizing cylinder 180 in the nip 150 (see for example the first flange 610A and second flange 610B shown in FIGS. 6, 7, 8, 10 and 13). The stabilizing cylinder 180 comprises a third hole 190 that passes through the length of the stabilizing cylinder 180 in the Z-axis direction. The diameter of the stabilizing cylinder 180 may be such that it provides enough mass to provide the structural support needed, but is not so large as to impede the motion of the joint 110.

In some embodiments, the stabilizing cylinder 180 is held in position by securing a second loop 160 though the first hole 120 of the distal lever 115 and the third hole 190 passing through the stabilizing cylinder 180, as well as a third loop 170 secured through the second hole 130 of the proximal lever 117 and the hole 190 passing through the stabilizing cylinder 180. This results in a triangular formation of loops, or triad 195, when viewing the joint 110 from the side. This triple system of loops (140, 160, and 170) and a stabilizing cylinder 180 provides additional stability to the joint 110, in particular by limiting rotational movement around the X-axis. These additional loops (second loop 160 and third loop 170), and the stabilizing cylinder 180, like the first loop 140 and the levers (115 and 117), are constructed of metal, plastic, ceramic, carbon fiber or a combination thereof.

Figure 3:
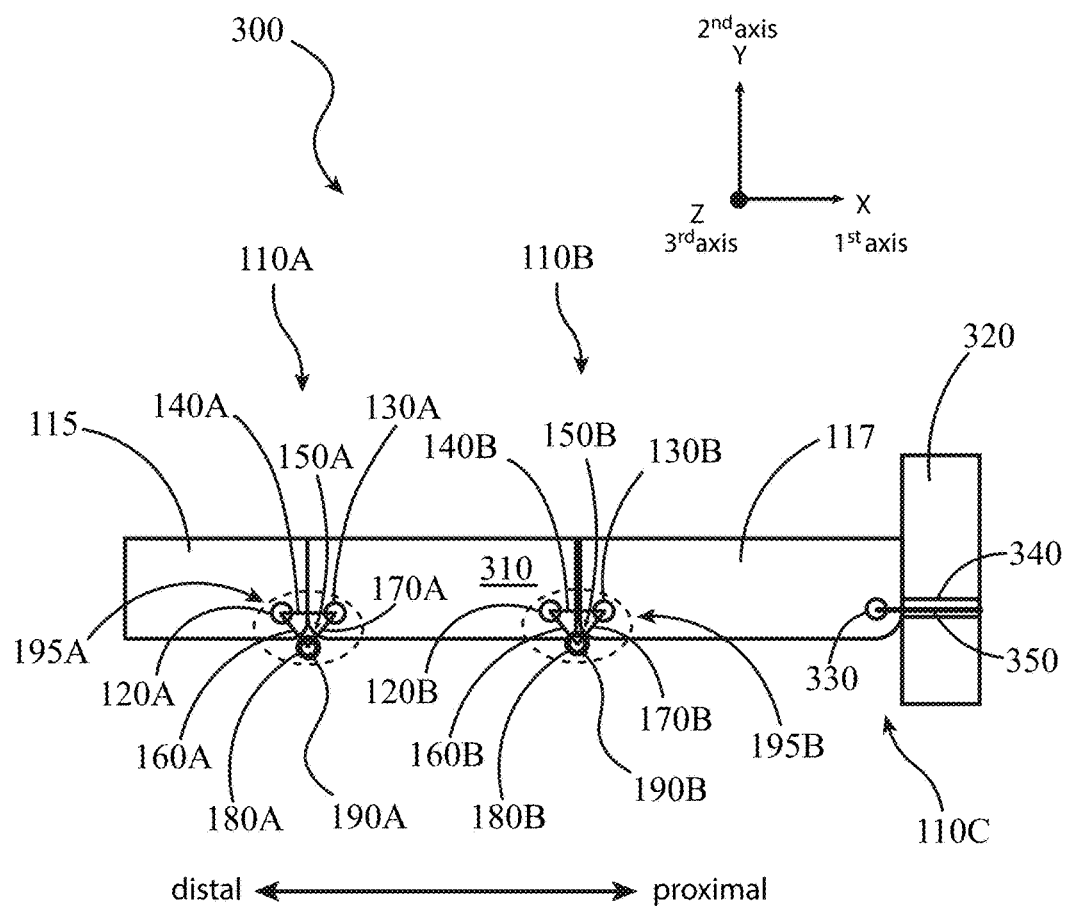
FIG. 3 is a front elevation view of one embodiment of the present disclosure of a digit of three levers, three hinges and a base.

Turning to FIG. 3, in some embodiments of the present disclosure is a digit 300 comprising a distal lever 115, a proximal lever 117 and a third lever 310, corresponding to a distal, intermediate and proximal phalange, respectively. The three levers (115, 117, and 310) are preferably aligned lengthwise along the X-axis, and each lever comprises a proximal end and a distal end. The proximal end of the distal lever 115 is adjacent to the distal end of the third lever 310, the proximal end of the third lever 310 is adjacent to the distal end of the proximal lever 117, and the proximal end of the proximal lever 117 is adjacent to a base 320. A first hole 120A of the distal lever 115 is preferably located in the proximal end of the distal lever 115, a second hole 130A of the third lever 310 is preferably located in the distal end of the third lever 310, a first hole 120B of the third lever 310 is preferably located in the proximal end of the third lever 310, a second hole 130B of the proximal lever 117 is preferably located in the distal end of the proximal lever 170, and a fourth hole 330 of the proximal lever 117 is preferably located in the proximal end of the proximal lever 117.

All five holes (120A, 120B, 130A, 130B, and 330) are preferably located in the palmar half of their respective levers (115, 117, and 310), and all five holes pass through the width of their respective levers in the Z-axis direction, and all are preferably aligned at about the same height in the Y-axis direction.

The proximal end and palmar side in the Z-axis direction of the distal lever 115 is rounded. The palmar side of both the proximal and distal ends, in the Z-axis direction, of both the proximal lever 117 and the third lever 310 are rounded.

The adjacent, rounded ends of the proximal end of the distal lever 115, and distal end of the third lever 310 form a first nip 150A, and the rounded sides of the adjacent third lever 310 and proximal lever 117 form a second nip 150B.

In some embodiments, the digit 300 forms a first joint 110A that secures the distal lever 115 to the third lever 310 by placing a first stabilizing cylinder 180A in the first nip 150A and securing a first loop 140A through the first hole 120A of the distal lever 115 and the second hole 130A of the third lever 310, securing a second loop 160A through the first hole 120A of the distal lever 115 and the third hole 190A of the first stabilizing cylinder 180A, and securing a third loop 170A through the second hole 130A of the third lever 310 and the third hole 190A of the stabilizing cylinder 180A.

The digit 300 further comprises a second joint 110B that secures the third lever 310 to the proximal lever 117 by placing a second stabilizing cylinder 180B in the second nip 150B and securing a first loop 140B through the first hole 120B of the third lever 310 and the second hole 130B of the proximal lever 117, securing a second loop 160B through the first hole 120B of the third lever 310 and the third hole 190B of the second stabilizing cylinder 180B, and securing a third loop 170B through the second hole 130B of the proximal lever 117 and the third hole 190B of the second stabilizing cylinder 180B.

Referring again to FIG. 3, in some embodiments, the digit 300 further comprises a third joint 110C that secures the proximal lever 117 to the base 320. The base 320 comprises an anchor 340, which in some embodiments is a hole or slot that passes through the base 320 in the X-axis direction. The anchor 340 is at about the same height in the Y-axis direction as the fourth hole 330. An attachment 350 secures the proximal lever 117 to the base 320 by passing the attachment 350 through the fourth hole 330 and the anchor 340.

In some embodiments, all three joints (110A, 110B, and 110C) of FIG. 3 provide biased motion in the palmar direction in the XY-plane, and also provide some motion in the dorsal direction of the XY-plane, some motion YZ-plane, some motion in the XZ-plane, as well as rotational motion around the X-axis.

In some embodiments, all three joints (110A, 110B, and 110C) of FIG. 3 limit motion in the XZ-plane to less than 1 degree, 2, 3, 4, or 5 degrees. In some embodiments, the joints (110A, 110B, and 110C) limit motion in the YZ-plane to less than 1 degree, 2, 3, 4, or 5 degrees.

In some embodiments of the present disclosure, the levers (115, 117, and 310) are plastic.

In some embodiments of the present disclosure, the levers (115, 117, and 310) and base 220 are produced by injection molding.

Figure 4:
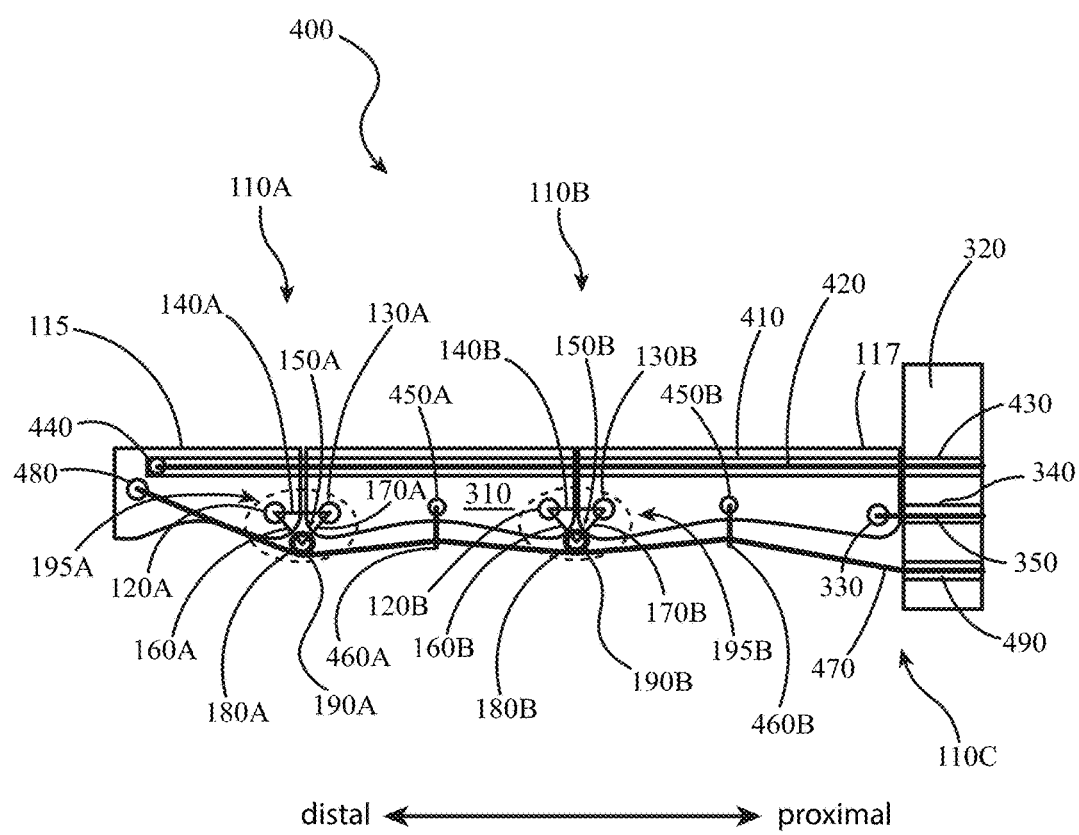
FIG. 4 is a front elevation view of one embodiment of the present disclosure of a digit of three levers, three hinges, and a base.

Turning to FIG. 4, some embodiments of a digit 400 contain a tension guide 410. This tension guide 410 may comprise a notch, indentation or other suitable means located in the dorsal half of each lever (115, 117, and 310), wherein the tension guide 410 is oriented in the X-axis direction. Through the tension guide 410, runs a tension cord 420, wherein the tension cord 420 is anchored on the proximal end of the digit 400 with the base 320, by a tension restraint 430, and wherein the tension cord 420 is anchored on the distal end of the digit 400 by securing the tension cord 420 in a tension hole 440, this tension hole 440 located in the distal third of the distal lever 115, also in the dorsal half of the distal lever 115, in the Y-axis direction. The tension guide 410 and the tension cord 420 run through the entire length in the X-axis direction of the third lever 310 and proximal lever 117. As stated, the tension guide 410 starts at the proximal end of the proximal lever 117 and terminates at the tension hole 440. This arrangement provides a constant force that pulls the digit 400, via the tension cord 420, into the fully extended position.

The tension cord 420 may comprise any suitable elastomer. Examples include but are not limited to elastic bands and bungee cord. The length required to provide a suitable force, is not elaborated here, and that design feature is known to one of skill in the art. The tension cord 420 may also comprise a filament and spring acting in series, or a single spring.

Referring to FIG. 4, in some embodiments, a fifth hole 450A is located about midway in the length of the third lever 310, in the palmar half of the third lever 310. A similar fifth hole 450B is located about midway in the length of the proximal lever 117, also in the palmar half of the proximal lever 117. Through the fifth holes (450A and 450B) are placed loops referred to as actuator guides (460A and 460B). The actuator guides (460A and 460B), guide an actuator cord 470 to which the amputee applies force, against the force exerted by the tension cord 420, to flex the digit 400.

The actuator cord 470 is firmly secured through an actuator hole 480, located in the distal end, at about midline in Y-axis direction, of the distal lever 115. The actuator cord 470 then passes over the first stabilizing cylinder 180A of the first joint 110A connecting the distal lever 115 to the third lever 310, passes through the first actuator guide 460A of the third lever 310, over the second stabilizing cylinder 180B of the second joint 110B connecting the third lever 310 to the proximal lever 117, passes through the second actuator guide 460B of the proximal lever 117, and finally passes through an actuator lead 490 located in the base 320.

In some embodiments, the actuator guides (460A and 460B), like the loops (140, 160, and 170) used to construct the joints (110A, 110B, and 110C), may be made of plastic, carbon fiber, metal, ceramic or a combination thereof.

In some embodiments, the actuator cord 470 is preferably a non-elastic cord, cable, wire, any other suitable non-elastic cord means, or a combination thereof.

In some embodiments, the relative lengths of the distal lever 115, the third lever 310, and the proximal lever 117 match the natural proportions of a human finger.

Figure 5:
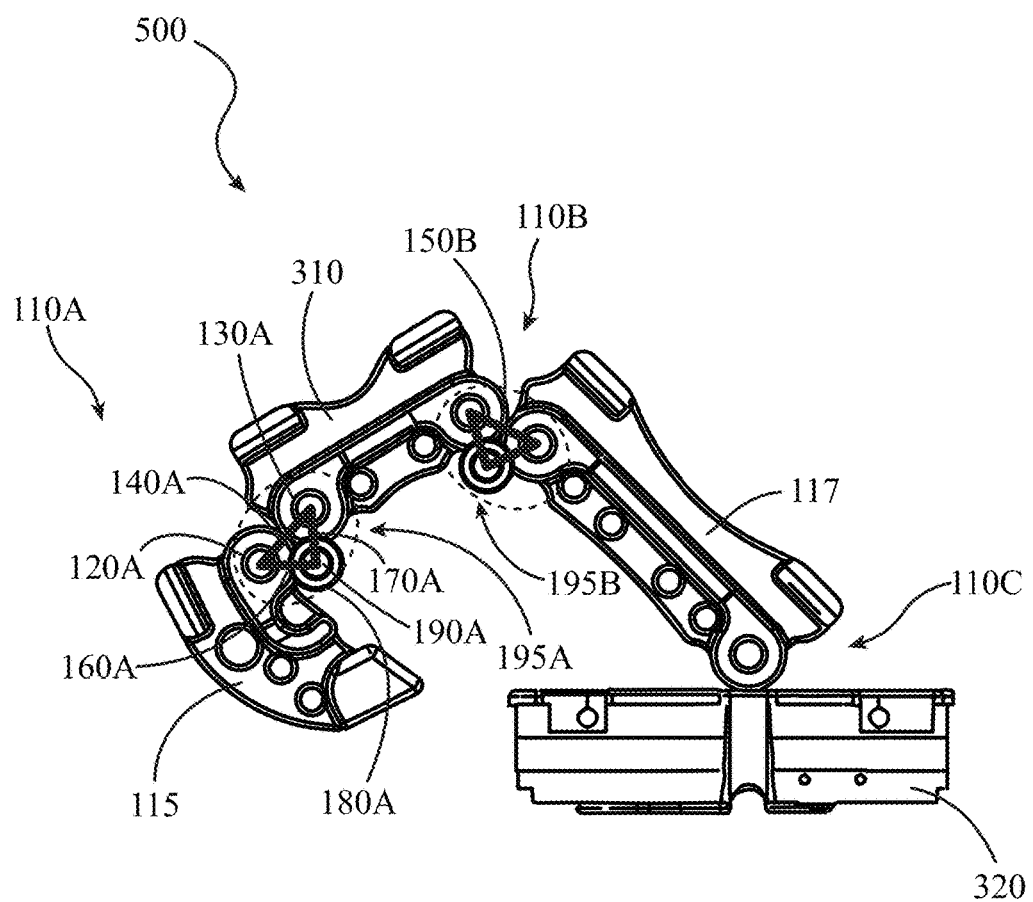
FIG. 5 is a front elevation view of one embodiment of a digit of the present disclosure.
Figure 6:
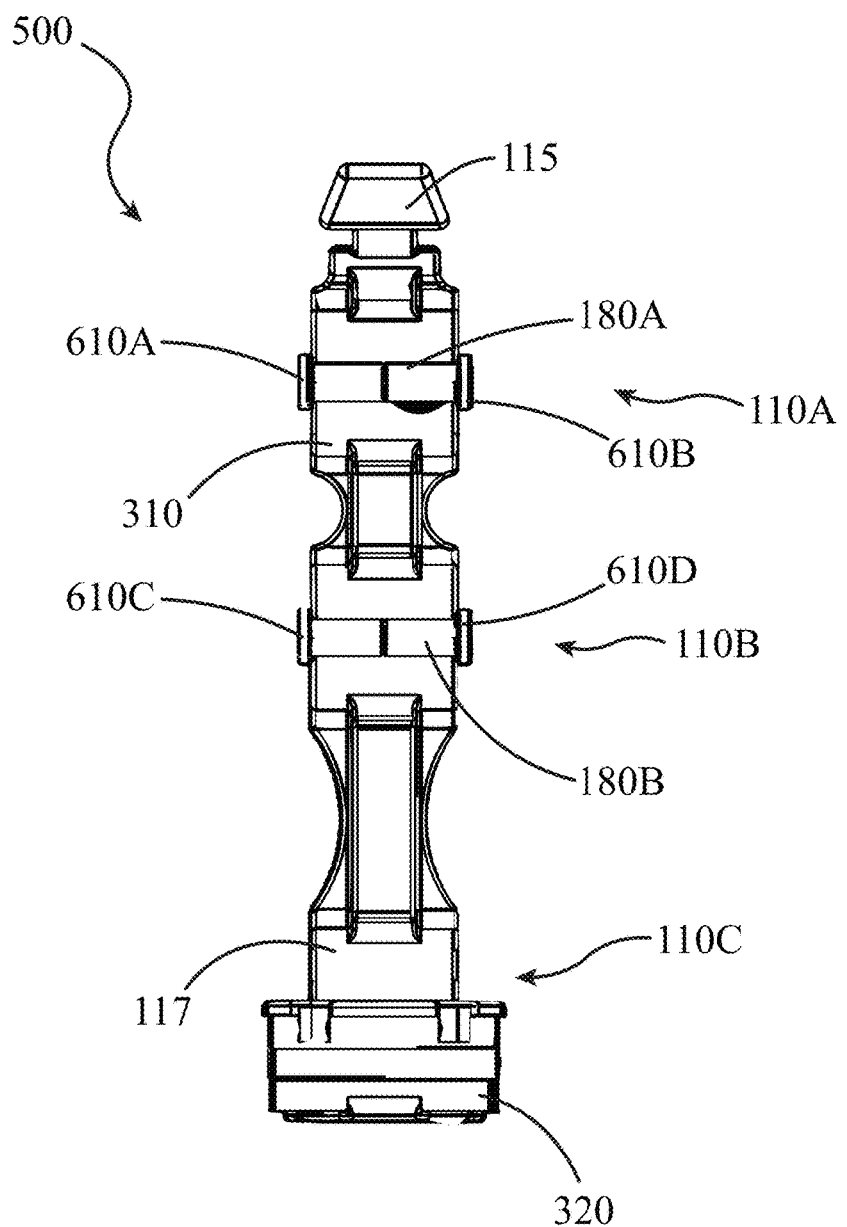
FIG. 6 is a bottom plan view of one embodiment of a digit of the present disclosure.
Figure 7:
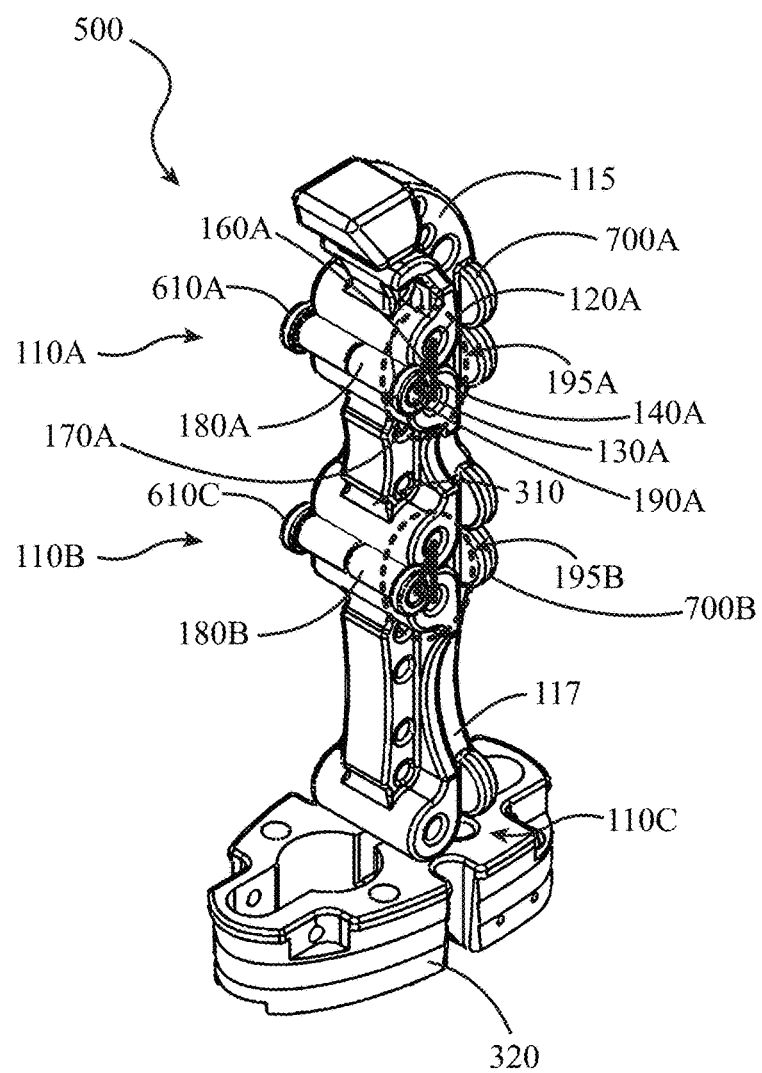
FIG. 7 is a perspective view of one embodiment of a digit of the present disclosure.
Figure 8:
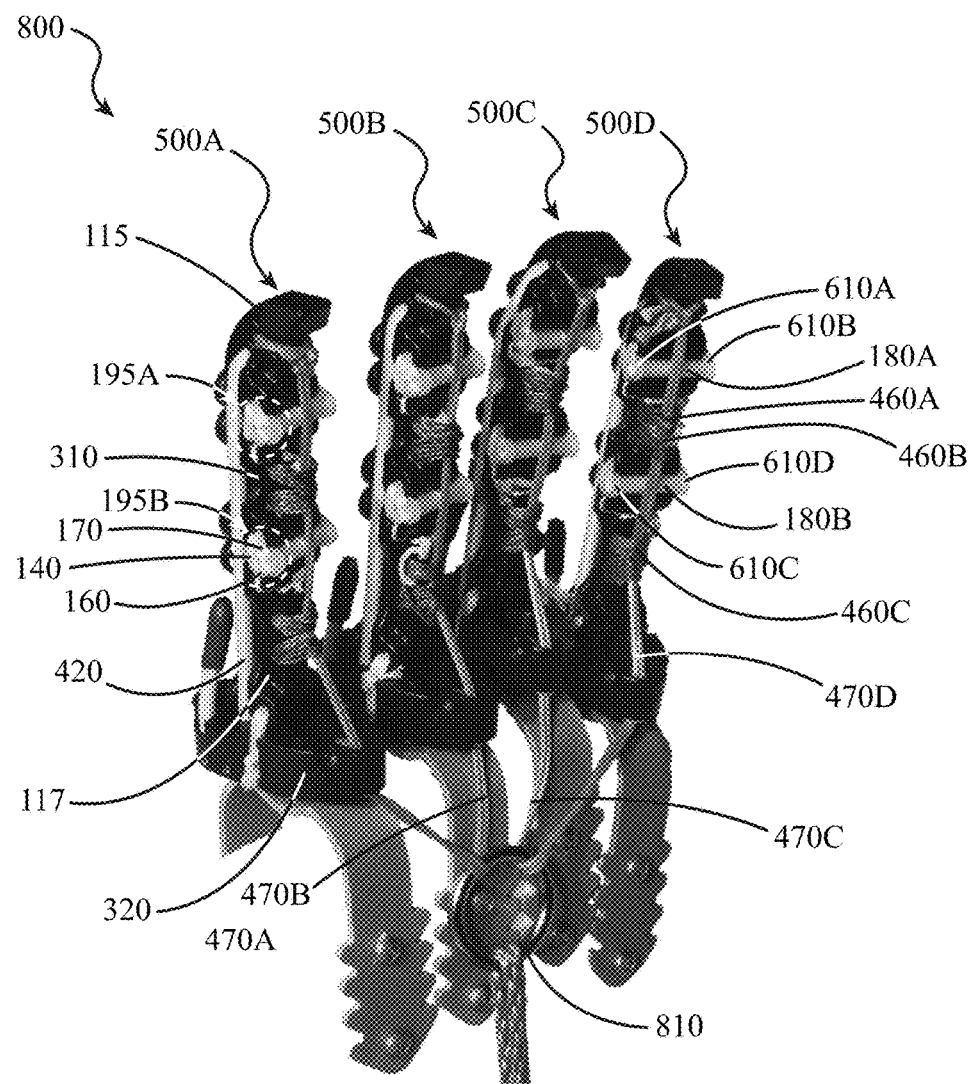
FIG. 8 is a perspective photograph of an actual prototype of the present disclosure, of four digits that comprise a partial hand amputation prosthetic device.
Figure 9:
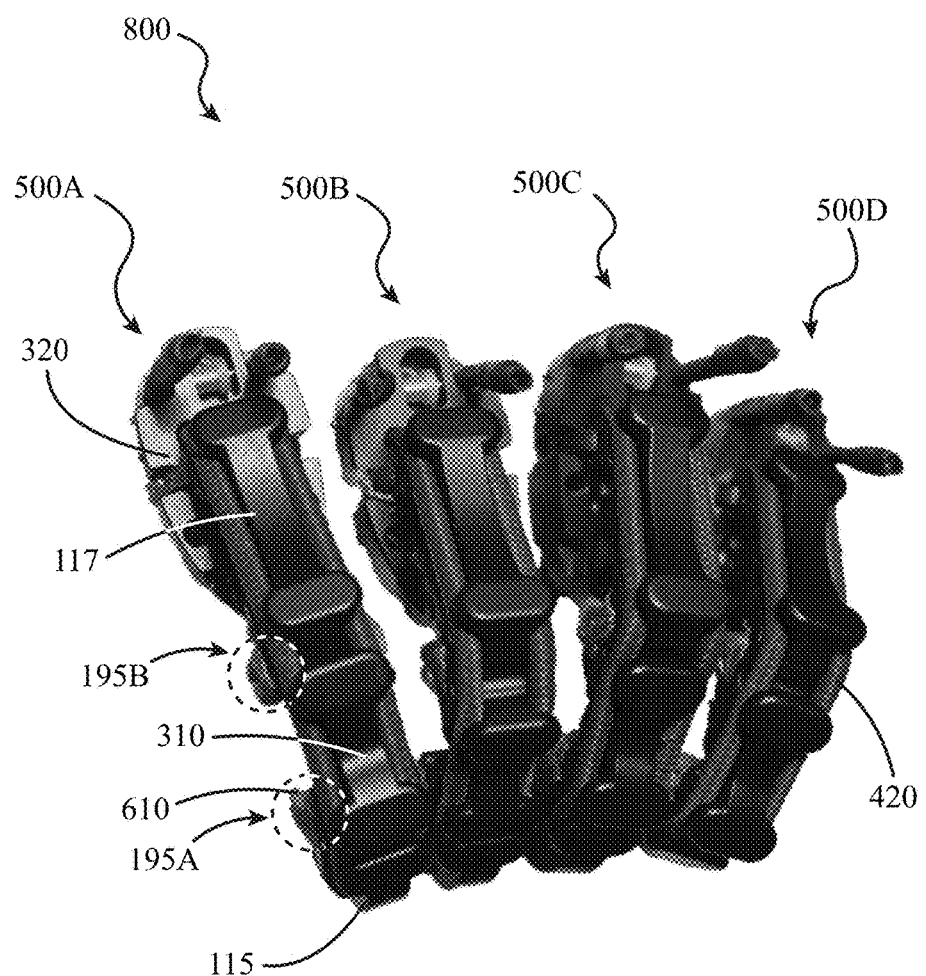
FIG. 9 is a perspective view photograph of an actual prototype of the present disclosure, of four digits in flexion.
Figure 10:
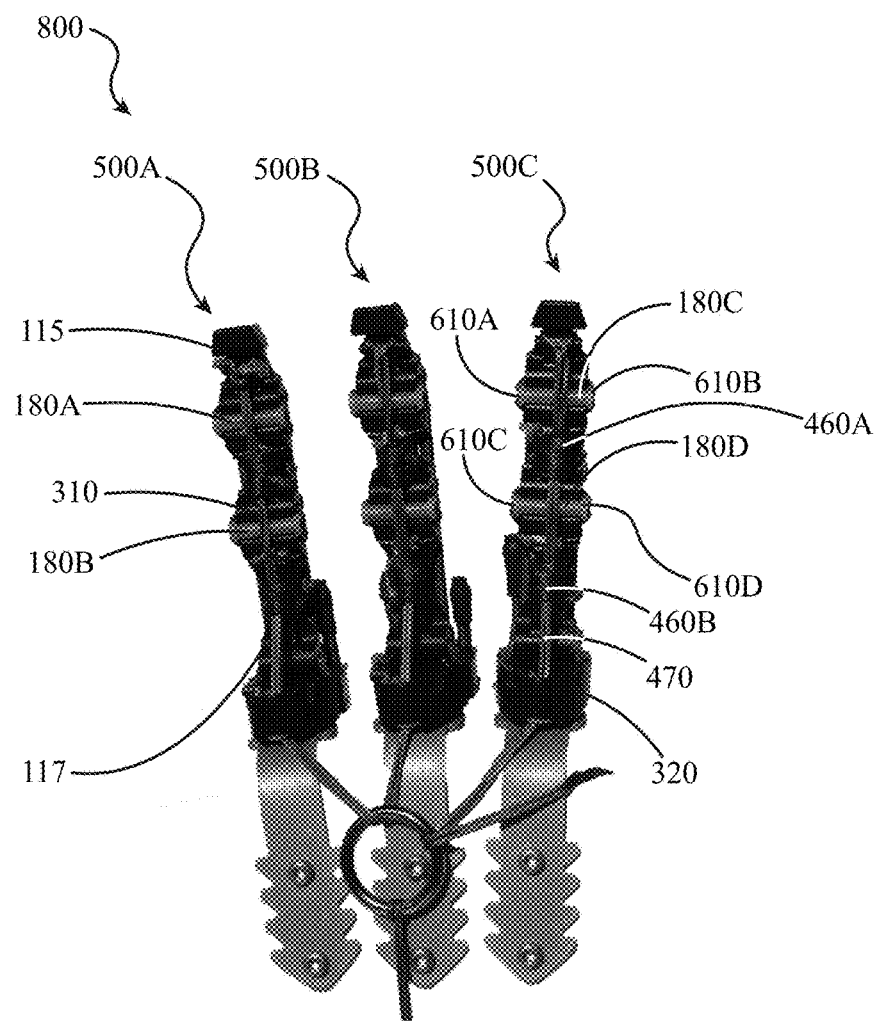
FIG. 10 is a bottom plan view photograph of an actual prototype of the present disclosure, illustrating an actuating cord and ring for flexing the digits.
Figure 11:
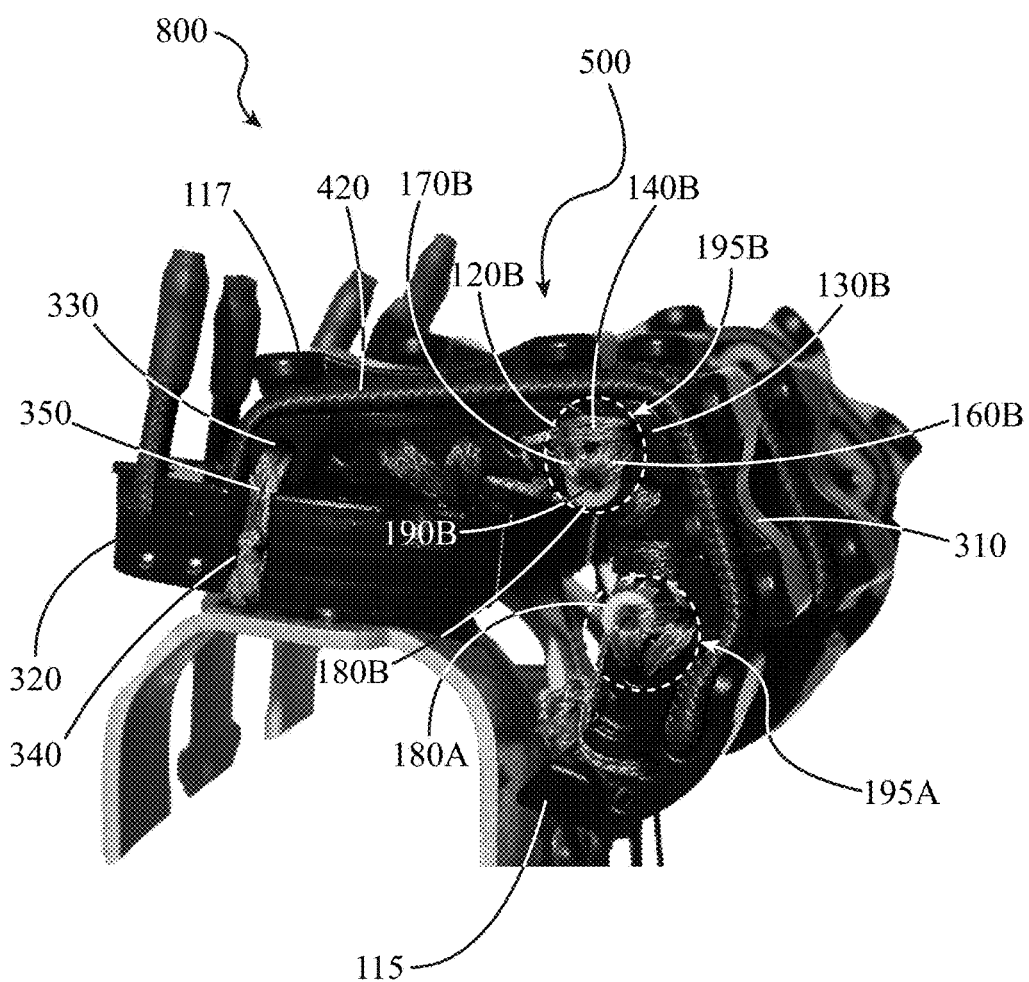
FIG. 11 is a front elevation view photograph of an actual prototype of the present disclosure, of four digits in flexion.
Figure 12:
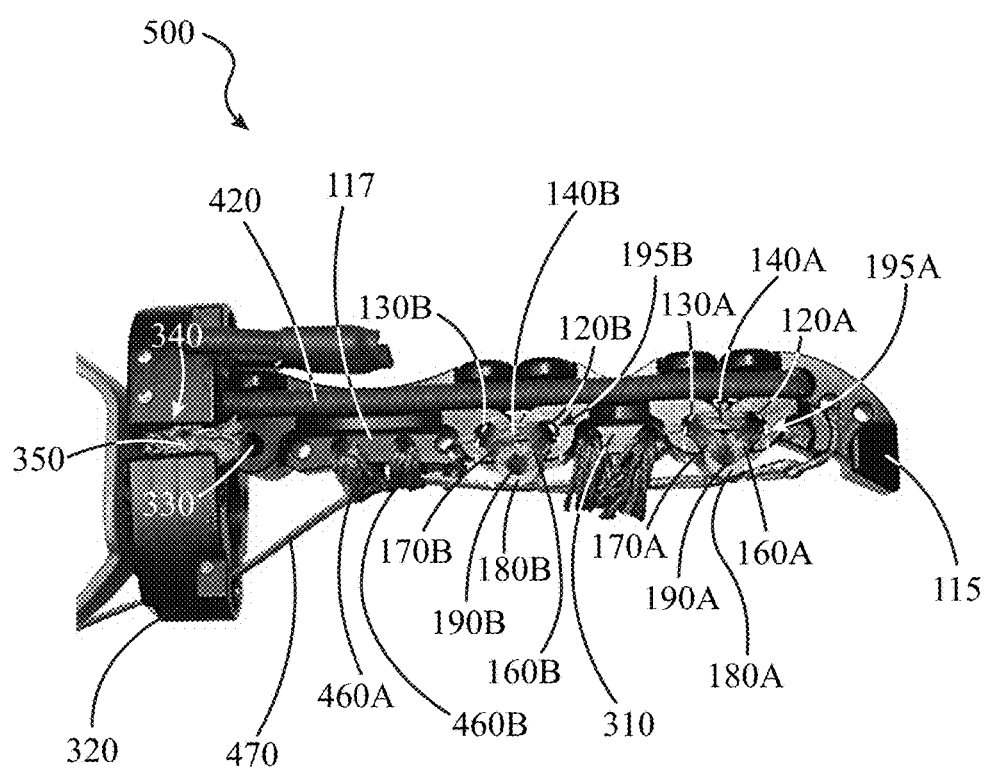
FIG. 12 is a front elevation view photograph of an actual prototype of the present disclosure, of a single digit in full extension.
Figure 13:
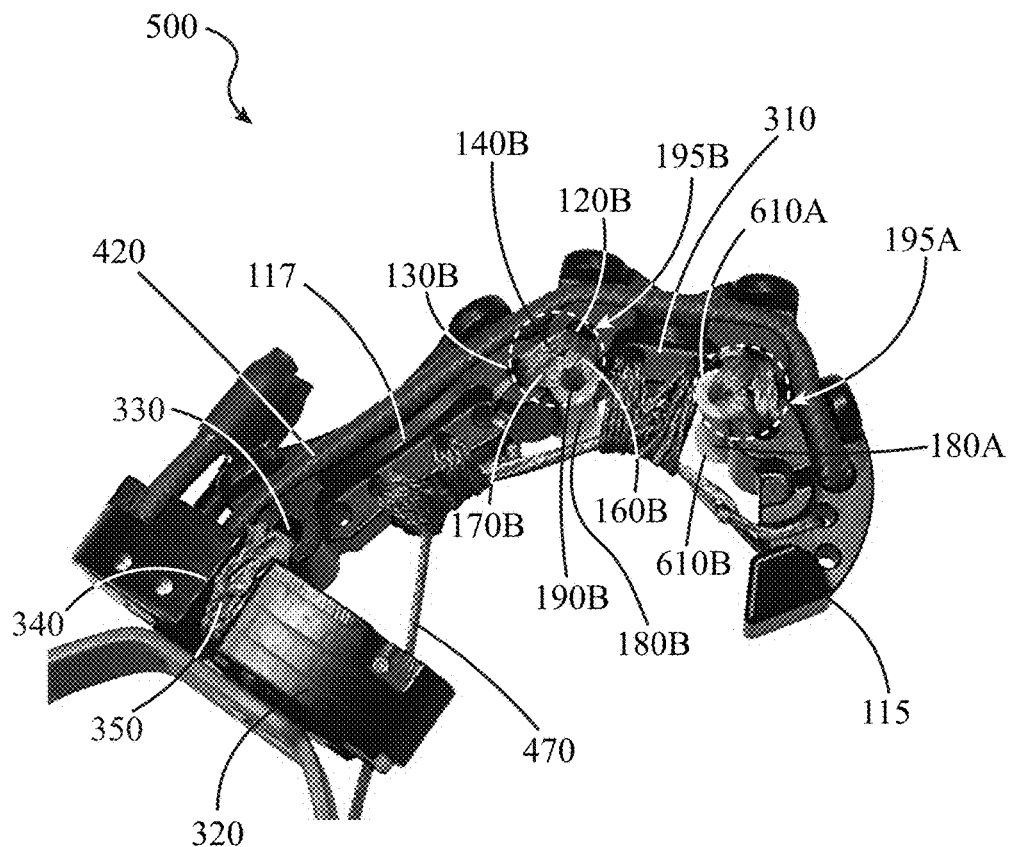
FIG. 13 is a front elevation view photograph of an actual prototype of the present disclosure, of a single digit in partial flexion.
Figure 14:
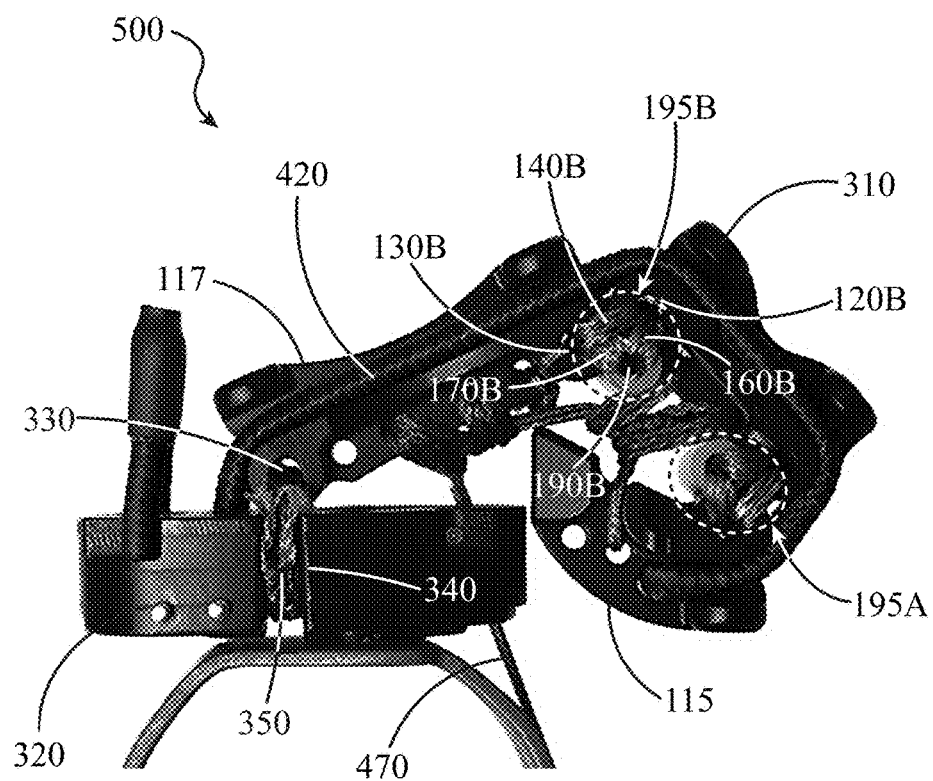
FIG. 14 is a front elevation view photograph of an actual prototype of the present disclosure, of a single digit in full flexion.

FIGS. 5-14 show different views of the prosthesis of this disclosure. FIGS. 5-6 are side and end views, respectively, of the prosthesis in full flexion. FIG. 7 is a perspective view of the prosthesis in an extended position. Flanges (700A and 700B) on each of the distal lever 115 and proximal lever 117 hold the tension cord 420 in position during digit 500 and lever (115, 117, and 310) movement. FIG. 8 depicts four digits (500A, 500B, 500C, and 500D) joined using a slip ring arrangement. The slip ring arrangement includes a ring 810 connected to multiple actuator cords (470A, 470B, 470C, and 470D), each of which independently operates a corresponding digit. FIG. 9 shows four digits (500A, 500B, 500C, and 500D) in flexion showing bases inclined with respect to the palm to achieve spherical prehension. FIG. 10 shows three digits (500A, 500B, and 500C) joined using a slip ring engagement. FIG. 11 shows three digits in flexion. The prosthesis replicates many of the elements of an anatomical hand. FIG. 12 shows a biomimetic digit 500 in full extension. FIG. 13 shows a biomimetic digit 500 in partial flexion. Finally, FIG. 14 shows a biomimetic digit 500 in full flexion. FIGS. 5-14 show digits 500 having stabilizing cylinders 180 placed in nips 150, and triangular formations of loops (140, 160, and 170) and holes (120, 130, and 190), or triads 195, where the triads 195 secure adjacent ends of levers (115, 117, and 310) to form joints 110, which allow some degree of motion in all three dimensions, including rotational movement around the digit's axis.

EXPERIMENTAL

The following examples are provided to illustrate certain aspects, embodiments, and configurations of the disclosure and are not to be construed as limitations on the disclosure, as set forth in the appended claims. All parts and percentages are by weight unless otherwise specified.

In one example, the three joints of a digit use a triad of ligament wraps (loops) made from high-strength, low-creep, braided Spectra® filament (80 lbf test>0.016" diameter, Innovative Textiles, Inc.) originally developed for competitive sport fishing. A single filament passes through holes in the stabilizer (cylinder) and each adjoining phalanx (lever), making ten (10) alternating passes around the joint, and its ends are secured to prevent loosening or slippage. Multiple filament passes form a composite bundle having a tensile strength exceeding that of the phalanx material. This triad construction admits planar flexion-extension movement while limiting lateral, off-axis bending and axial twist to levels consistent with the anatomical finger. Some lateral bend and axial twist are desirable as they help distribute tractive forces over the surface of objects, significantly increasing grasp quality. This configuration is called "digit circumduction" in the anatomical hand and not currently in use in any other existing articulating digits or multi-articulating hands—body-powered or otherwise—that allow for beneficial digit circumduction.

Two passes of nylon jacketed elastic "bungee" cord on each digit's dorsal side act as extensors (tension cord). Their tension level is adjusted to overcome cosmetic cover stiffness and flexor tendon drag to ensure full digit extension. Two passes of Spectra® cord (150 lbf test>0.025" diameter, Ashaway, Inc.), specially braided for professional kite fighting and sporting equipment, form the flexor tendon on the digit's volar side. Entering the digit through a special low-wear ceramic textile guide in the base, this flexor tendon (tension cord) bridges the proximal and middle phalanges and attaches directly to the distal phalanx. Tendon guides (tension guides) made from open coils of Spectra® filament (100 lbf test>0.022" diameter, Innovative Textiles, Inc.) attach to the proximal and middle phalanges (levers), analogous to the annular and cruciform fibrous sheaths that transfer force to the phalangeal segments in the anatomical finger. These guides also minimize frictional drag on the tendon (actuator cord) analogous to the synovial sheath. Adjusting the length and attachment locations of these "synovial coils" on each phalanx controls the sequencing of joint movements as the digit flexes.

The prosthesis design of this disclosure intentionally permits selection of attachment points that initiate flexion at the base of the digit and then move proximally from the distal phalanx. If an object is not encountered as the digit sweeps, it closes to establish "key grip" against an opposition thumb, one of the most important and useful prehension patterns. If an object is encountered during sweep, digit flexion begins at the distal end, curling back against the object and drawing it towards the base for strong, stable grasp.

To facilitate low-cost manufacture, strict injection molding criteria were imposed on the base and phalange designs to use standard two-part "mud" bases without expensive secondary slides. The parts are also designed for "family molding" in one injection cycle to maximize manufacturing efficiency and minimize material waste per shot. The net result is a considerable reduction in tooling and final part cost. For this effort, parts were fabricated by the FirstCut® division of ProtoMold® from Delrin® 150 acetal homopolymer (DuPont) using state-of-the-art high-speed conventional machining optimized for rapid prototype fabrication. While cost effective within the scope of this developmental work, part pricing for components fabricated this way is not viable for long-term commercial production.

At least three distinct digit lengths are needed to avoid "broom hand" (i.e., all digits mounted on a straight knuckle line and having the same length—like a broom.) These phalangeal segments permit various combinations to obtain different overall digit lengths without additional tooling cost or complexity. The distal phalanx serves as digit tip with articulation on its proximal end only, along with flexor tendon and extensor attachment points; it is common to all sizes. Table 1 shows possible constructions.

TABLE 1

Possible Overall Digit Lengths Based on Phalanx Combinations

| Phalanx | Length | Index (2)† & Ring (4) | Middle (3) | Small (5) |
|---|---|---|---|---|
| Proximal | 1.13 in | x1 | x2 | |
| Middle | 0.75 in | x1 | | x2 |
| Distal | 0.62 in | x1 | x1 | x1 |
| Digit Length | | 2.50 in | 2.88 in | 2.12 in |

The digit mounting means disclosed herein can better serve partial hand amputees. Instead of a single composite "rack" that forces digits into an unnaturally straight line as currently used in existing products, the digit mounting means of this disclosure can provide a more versatile strap system offering several advantages. Each digit is mounted on a single metal structural strap folded into a saddle or "taco" shape that is affixed on both the volar and dorsal aspects of a partial-hand prosthetic shell for increased strength and rigidity. Each strap's ends are designed with serrations that allow it to be strongly secured using standard fiberglass or carbon fiber layup techniques commonly employed in the field; holes are provided for tinner's rivets if preferred (another common attachment method.) Each strap is independently shapeable by the prosthetist to position each digit optimally on an arc within the anatomical hand space rather than forcing them into an artificial, non-optimal line. As the straps are rigidly integrated into the prosthetic shell and cannot be easily removed, the digit bases are designed to attach with a screw accessible from the front, permitting easy modular replacement if necessary. Moreover, the flexion plane of each digit can be oriented independently with respect to the palm for improved spherical prehension. This innovation can markedly benefit amputees having excessive scarring, adipose tissue, bulbous amputations, or where the prosthetist must orient digit movements to optimally interface with remaining anatomical digits for coordinated useful grasp.

TABLE 2

Laboratory Testing Results

| | | |
|---|---|---|
| Physical Parameters | Moving Length | 2.88 inches |
| | Total Weight | 1.0 ounce (including strap mount |
| | Full Curl Tendon Tension | 7.5 lbf (no load, clear swing trajectory) |
| | Lateral Circumduction Angle | 1.4 inches (no load, clear swing trajectory) |
| | Axial Twist Angle | ±18° on axis |
| Laboratory Performance | Max Lift Load: "Hook Grip" | 20 lbf (1.0 inch diameter handle) |
| | Sustaining Tendon Tension | 27 lbf (forward force ratio [FFR]: 0.74) |
| | Max Reverse Bending Load | 3.1 lbf (at extreme digit tip) |
| | Flexion Cycle Life to 1$^{st}$ Failure | 637K tendon failure, replaced & continued |
| | Extended Cycle Life | >1.1 MM test terminated, no failure |

To ensure "worst case" cantilever loading conditions, laboratory testing was carried out using the middle digit configuration given in Table 1; test results are outlined in Table 2. Hook and key grip prehension forces were chosen for measurement as these patterns are less subjective and 1) are relatively easy to instrument, 2) rely directly upon the digit mechanism itself, and 3) don't depend upon the object being grasped, its orientation, cosmetic cover characteristics, etc.

To perform cycle life testing, a dedicated-purpose apparatus was constructed. Destructive cycle testing showed units attaining an average of 637K grasping cycles before tendon failure. Replacing the tendon is trivial; in one case this was done and testing extended. In this case, all other structures of the digit—excluding the tendon—survived in excess of 1.1 MM cycles before testing was terminated. Measurements of lateral bending tip displacement and axial twist taken before and after cycling showed no change (0.25" off midline and ±18° on-axis twist, respectively) indicating the ligament wrap triads did not stretch or loosen during the test. Subsequent teardown and examination in the laboratory found minor compression set but no fraying of the ligament wraps in contact with the phalanges, mild localized polishing on phalanx articulation surfaces, and some transfer of tendon material to the inside of the synovial coil guides (accounting for the tendon's failure); no other discernible wear was found.

Configured as a Gang-of-Four (a full partial-hand prosthesis), best operation was achieved joining digits as pairs and passing their common flexor tendon through a low friction slip ring. This arrangement behaves similar to a conventional whiffle tree, equilibrating flexion and grasping force, but with less excursion loss. Additional development is required to implement a commercially viable whole-hand design. Several lessons were learned during the work out lined above:

(1) Replicating structural elements of the anatomical finger to create a biomimetic prehensile digit having comparable appearance, movement, and prehension force envelope is possible.

(2) Synthetic filaments can perform analogous to the ligaments, tendons, fibrous sheaths, and synovial sheaths found in the anatomical digit, achieving excellent service life while simultaneously reducing cost, weight, mechanical complexity, and eliminating the need for lubrication.

(3) The triad ligament wrap construction described here achieves outstanding articulation stability and limits both lateral bending and axial twist to acceptable levels.

(4) Allowance for limited lateral bending and axial twist enhances the digit's ability to adaptively grasp by permitting surface contact forces and joint torques to equilibrate.

(5) Incorporating digits into assistive appliances as separate components—not grouped onto a common rack or bar—enables the prosthetist to better position the digits within the anatomical hand space for optimal grasping function and cosmesis.

(6) A quasi-whiffle tree connection for multiple digit flexor tendons (i.e. a slip-ring arrangement) provides a reasonable balance of flexor tendon excursion and force for each digit.

A number of variations and modifications of the disclosure can be used. It would be possible to provide for some features of the disclosure without providing others.

For example in one alternative embodiment, the holes 120 and 130 pass along the X-axis at least substantially through the first distal lever 100 and second proximal lever 110. In this manner, the looped cord passes through each of the adjoining first distal and second proximal levers rather than through the sides of the first distal and second proximal levers as shown in FIG. 1.

The present disclosure, in various aspects, embodiments, and configurations, includes components, methods, processes, systems and/or apparatus substantially as depicted and described herein, including various aspects, embodiments, configurations, subcombinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. An external prosthetic biomimetic digit comprising:
   a first phalange comprising a proximal end, a palmar side, a dorsal side, and a first hole positioned towards the proximal end of the palmar side of the first phalange;
   a second phalange comprising a distal end, a palmar side, a dorsal side, and a second hole positioned towards the distal end of the palmar side of the second phalange; and
   a stabilizing cylinder comprising a length, a diameter, and a third hole passing through the length, wherein:
   the proximal end is positioned adjacent to the distal end,
   the palmar side of the proximal end of the first phalange is rounded to form a first arc,
   the palmar side of the distal end of the second phalange is rounded to form a second arc such that the first arc and the second arc form a nip,
   the stabilizing cylinder is positioned in the nip, and
   the proximal end is movably attached to the distal end by a first loop secured through the first hole and the second hole, a second loop secured through the first hole and the third hole, and a third loop secured through the second hole and the third hole such that the first loop, the second loop, and the third loop form a triangular formation.

2. The digit of claim 1, wherein the stabilizing cylinder further comprises:
   a first end and a second end;
   a first flange positioned at the first end; and
   a second flange positioned at the second end.

3. The digit of claim 1, further comprising:
   a base comprising a third hole; and
   a fourth loop, wherein:
   the second phalange further comprises a proximal end and a fourth hole positioned towards the proximal end of the palmar side of the second phalange, and
   the proximal end of the second phalange is movably attached to the base by the fourth loop secured through the third hole and the fourth hole.

4. The digit of claim 1, further comprising:
   a first tension guide positioned along the dorsal side of the first phalange;
   a second tension guide positioned along the dorsal side of the second phalange; and
   a tension cord comprising a first end and a second end, wherein:
   the first phalange further comprises a distal end with a fifth hole positioned towards the dorsal side and the distal end of the first phalange,
   the base further comprises a sixth hole,
   the tension cord is positioned in the first tension guide and the second tension guide,
   the first end of the tension cord is secured to the fifth hole, and
   the second end of the tension cord is secured to the sixth hole.

5. The digit of claim 1, further comprising:
   a cord comprising a first end and a second end, wherein:
   the first phalange further comprises a seventh hole positioned towards the palmar side and the distal end of the first phalange,
   the base further comprises an eighth hole,
   the first end of the cord is secured to the seventh hole,
   the second end of the cord is secured to the eighth hole, and
   the cord passes over the stabilizing cylinder.

* * * * *